(12) United States Patent
Golder et al.

(10) Patent No.: US 7,298,127 B2
(45) Date of Patent: Nov. 20, 2007

(54) PARTICLE DETECTION

(75) Inventors: Roger Francis Golder, Ely (GB);
Roger Fane Sewell, Newnham (GB);
Danielle Emma Toutoungi, Cambridge (GB)

(73) Assignee: Smiths Detection - Waterford Limited, London (GB)

( * ) Notice: Subject to any disclaimer, the term of this patent is extended or adjusted under 35 U.S.C. 154(b) by 0 days.

(21) Appl. No.: 10/595,082

(22) PCT Filed: Sep. 3, 2004

(86) PCT No.: PCT/GB2004/003755

§ 371 (c)(1),
(2), (4) Date: Mar. 6, 2006

(87) PCT Pub. No.: WO2005/024393

PCT Pub. Date: Mar. 17, 2005

(65) Prior Publication Data

US 2006/0164094 A1    Jul. 27, 2006

(30) Foreign Application Priority Data

Sep. 5, 2003   (GB)   ................ 0320809.7

(51) Int. Cl.
*G01N 27/00* (2006.01)
*G01N 27/60* (2006.01)
*G01N 37/00* (2006.01)
*G01N 15/00* (2006.01)
*G01N 15/02* (2006.01)
*G06F 19/00* (2006.01)

(52) U.S. Cl. .................... 324/71.1; 324/71.4; 324/452; 73/28.02; 73/865.5; 702/29; 356/335

(58) Field of Classification Search ............... 324/71.1, 324/452, 71.4; 73/28.02, 865.5; 702/29; 356/335
See application file for complete search history.

(56) References Cited

U.S. PATENT DOCUMENTS

| | | | | |
|---|---|---|---|---|
| 3,763,428 A | * | 10/1973 | Preist | ......................... 324/71.1 |
| 3,852,768 A | * | 12/1974 | Carmichael et al. | ........... 347/81 |
| 4,117,715 A | * | 10/1978 | Hoenig | ....................... 73/28.01 |
| 5,214,386 A | * | 5/1993 | Singer et al. | ................ 324/452 |
| 6,553,849 B1 | * | 4/2003 | Scofield et al. | ............. 73/865.5 |
| 6,862,536 B2 | * | 3/2005 | Rosin | ........................... 702/29 |

\* cited by examiner

*Primary Examiner*—Walter Benson
*Assistant Examiner*—Amy He
(74) *Attorney, Agent, or Firm*—Foley & Lardner LLP

(57) ABSTRACT

Particle detection and characterizing apparatus has an insulating tube along which the particles flow. Five electrodes spaced along the outside of the tube are connected via amplifiers to a processor arranged to measure the charge on the particles. The apparatus also includes a laser and photomultiplier tube arranged to measure the size of the particles so that the nature of the particles can be characterized from their electrical charge and size.

7 Claims, 7 Drawing Sheets

PARTICLE DETECTION

This invention relates to particle detection and characterisation.

Various techniques are used to detect and identify small airborne particles, such as ion mobility spectrometry, cyclone collection or the like. These suffer form various disadvantages especially when detecting small particles, such as biological particles.

It is an object of the present invention to provide an alternative apparatus and method of characterising particles.

According to one aspect of the present invention there is provided apparatus for characterising particles including first means for determining the electrical charge on the particles and second means for determining a second characteristic of the particles, the apparatus being arranged to provide an indication of the nature of the particles according to the charge and the second characteristic.

The second characteristic is preferably size and the means for determining size may be optical means. The apparatus may include a plurality of the first means for one of the second means. The first means may include means defining a pathway for the particles and a plurality of electrodes spaced along the pathway arranged to provide an electrical output as the particles pass along the pathway. The means defining the pathway preferably includes a tube. There are preferably five electrodes spaced along the pathway. The outermost electrodes may be grounded, the two electrodes adjacent the outermost electrodes may be connected together and a signal may be derived from the difference between the central electrode and the two interconnected electrodes. The tube may have an internal diameter of about 0.5 mm. The apparatus preferably includes means preventing particles greater than about 10 μm from entering the tube.

According to another aspect of the present invention there is provided a method of characterising particles including the steps of measuring the electrical charge on the particles, measuring a second characteristic of the particles and providing an output indicative of the nature of the particles from the charge and the second characteristic.

The second characteristic is preferably size.

According to a third aspect of the present invention there is provided apparatus for measuring the charge on a particle including a tube along which the particle is arranged to flow, first and second outer electrodes towards opposite ends of the tube, third and fourth electrodes adjacent the first and second electrodes respectively, a fifth electrode between the third and fourth electrodes, means connecting the first and second electrodes to ground, means connecting the third and fourth electrodes with one another and to measuring means, and means connecting the fifth electrode to the measuring means, the measuring means being arranged to subtract the signals on the third and fourth electrodes from the fifth electrode to derive a signal indicative of the charge on the particle.

Particle characterisation apparatus according to the present invention, will now be described, by way of example, with reference to the accompanying drawings, in which.

Figure 1:
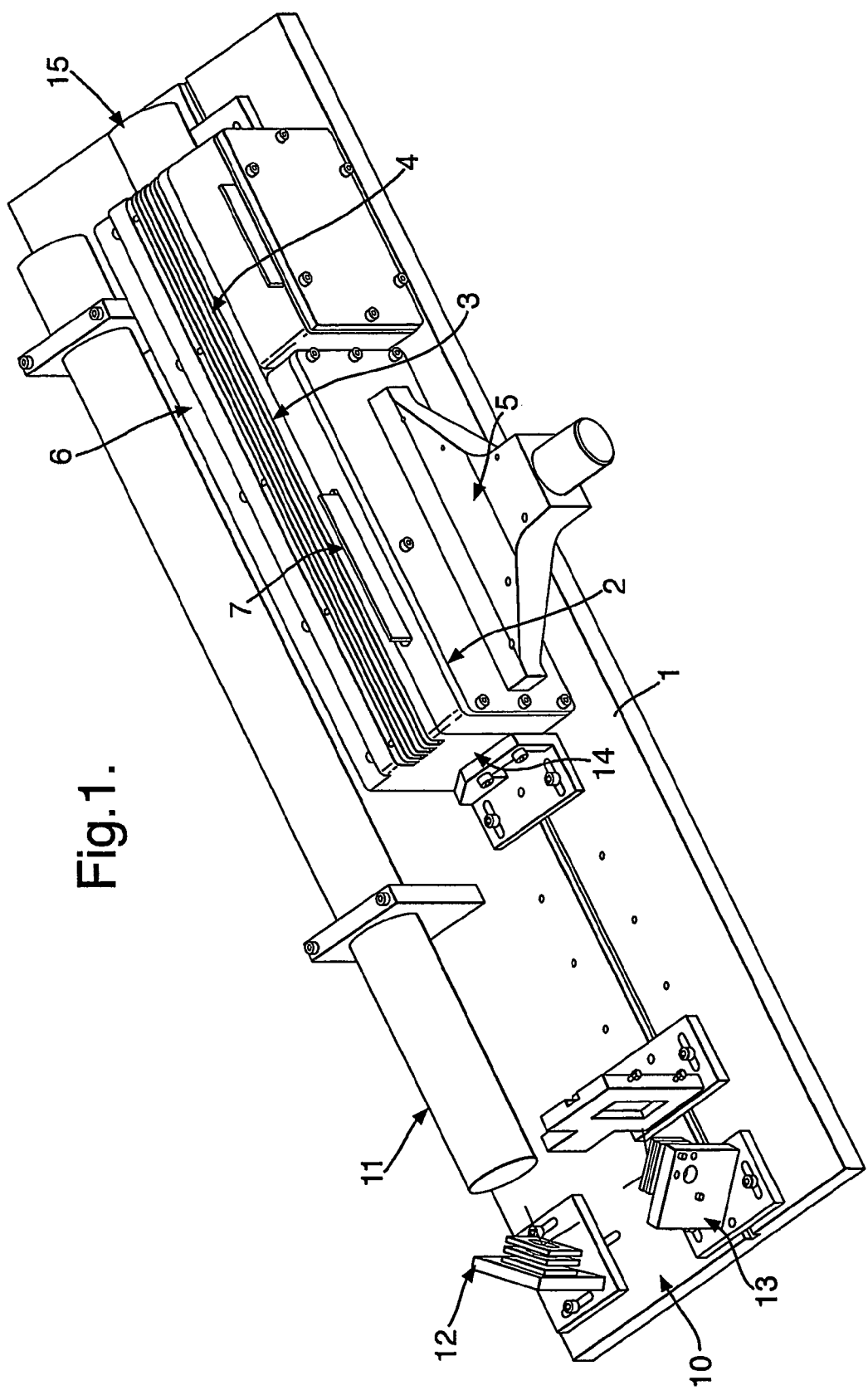
FIG. 1 is a perspective view of the apparatus.

With reference first to FIG. 1, the apparatus includes a metal base board 1 on which is mounted a support assembly 2 of generally rectangular shape and having a longitudinally-extending recess 3 in which is received a charge-measuring assembly 4 with cooling fins on its upper surface. The support assembly 2 has a box-like inlet structure 5 on one side providing a plenum chamber for air drawn to the inlet side of the charge-measuring assembly. A box-like outlet structure 6 extending along the opposite side of the charge measuring assembly 4 includes a plenum chamber and an outlet opening on the lower surface of the board through which air can be pumped away from the apparatus. A third structure 7 provides electrical connection to the assembly 4. Further details of the charge-measuring assembly 4 are given below.

The board 1 also supports particle size measuring means in the form of an optical laser arrangement indicated generally by the numeral 10. The arrangement includes a laser tube 11 mounted horizontally on the board 1 to extend parallel to the support assembly 2. Two inclined mirror assemblies 12 and 13 are oriented to direct the beam of radiation emerging from one end of the tube 11 axially of the charge measuring assembly 4 and, in particular, the beam of radiation is incident on a window 14 in one end of the charge measuring assembly and passes along its length to emerge from its other end and be absorbed in an optical beam dump 15.

Figure 2:
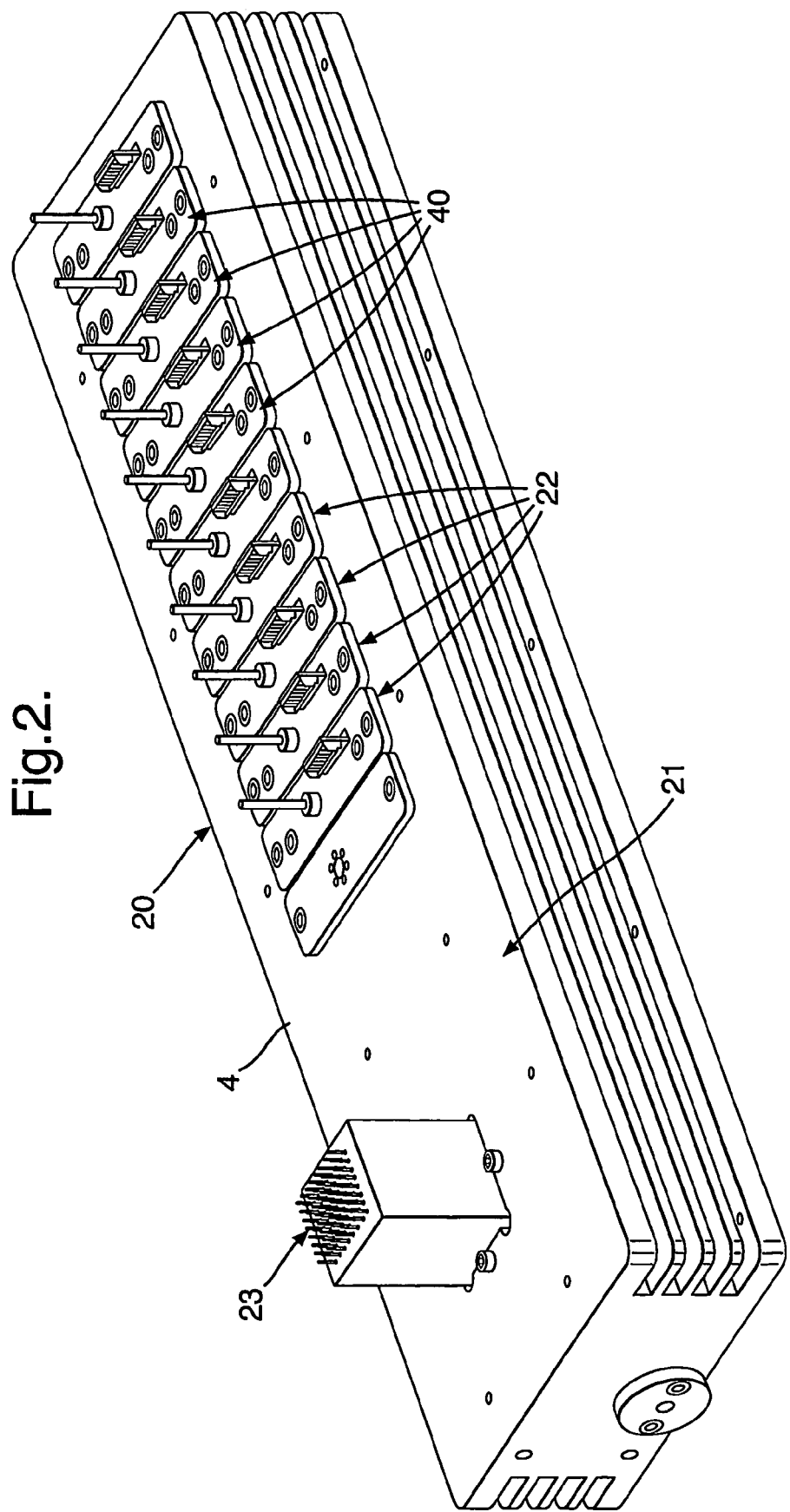
FIG. 2 is a perspective view of the front side of the charge-measuring assembly.
Figure 3:
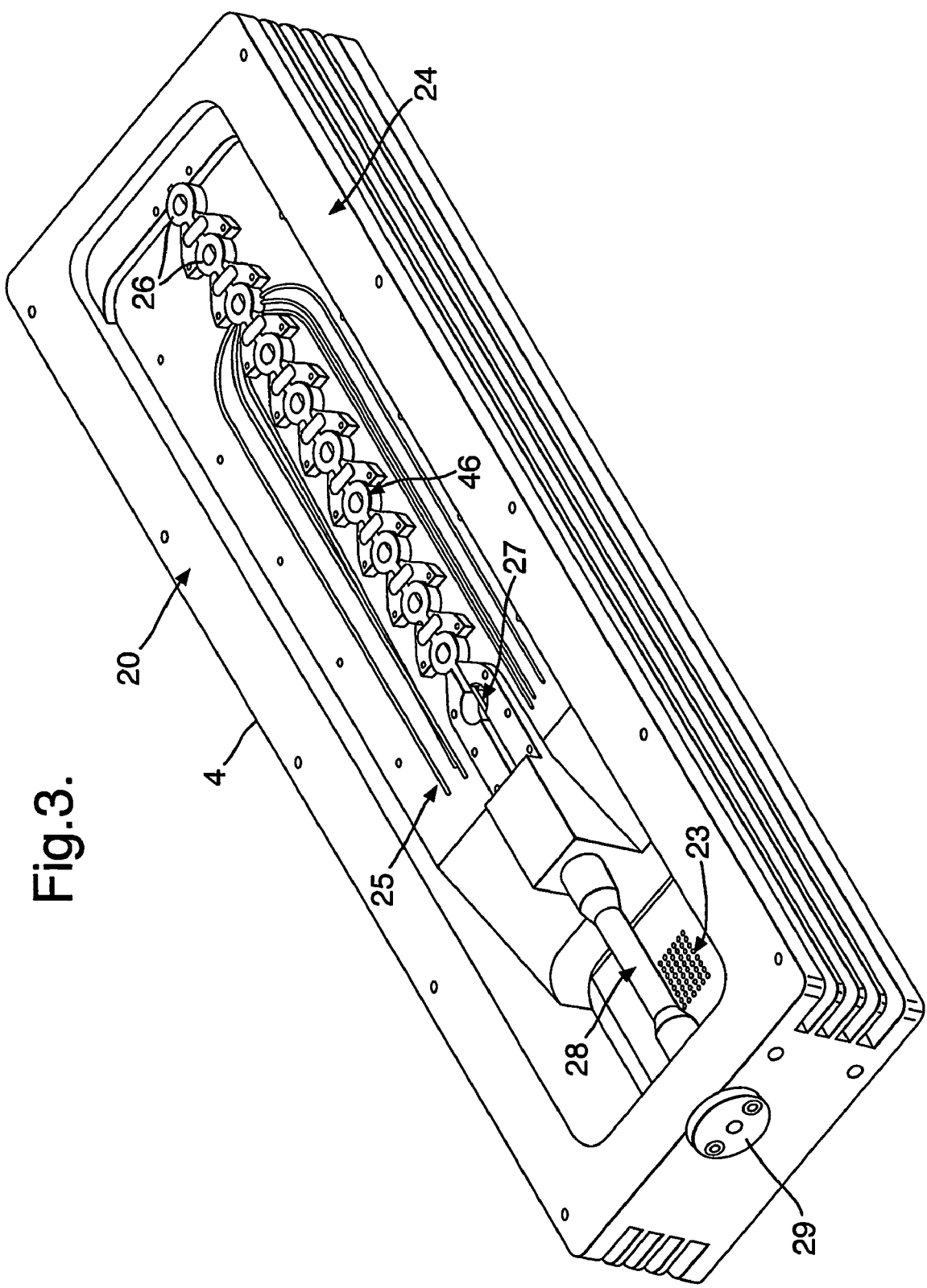
FIG. 3 is a perspective view of the rear side of the charge-measuring assembly.

The charge measuring assembly 4 is shown in greater detail in FIGS. 2 and 3. It comprises a rectangular metal block 20 with a forward surface 21 in which ten recesses 22 extend laterally of the block side-by-side towards its right-hand end. A photo multiplier tube (PMT) 23 is mounted on the forward surface towards the left-hand end of the block 20 for measuring the size of the particles. The rear surface 24 of the block, as shown in FIG. 3, has a shallow recess 25 extending along most of its length and has ten circular apertures 26 opening into the recess aligned with respective ones of the recesses 22 in the forward surface 21. A groove 27 providing a laser pathway extends diametrically across the apertures 26. The lower end of the groove 27, as represented in FIG. 3, opens into the window 14. At its other end, the groove 27 opens into a tubular guide 28 extending to the end of the block 20 and terminated by a coupling 29 to which the optical beam dump 15 is connected.

Figure 4:
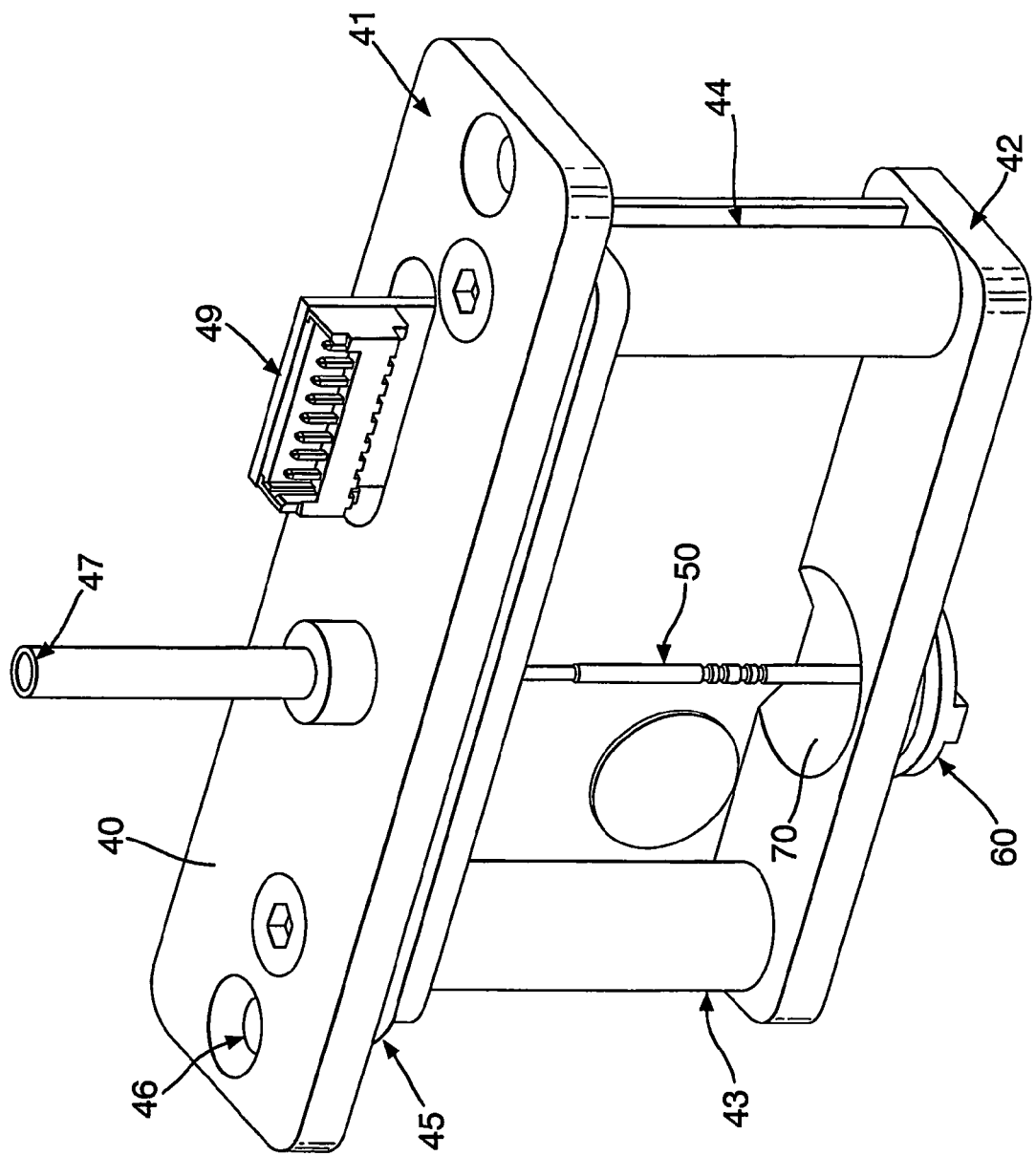
FIG. 4 is a perspective view of a single charge-measuring unit within the assembly of FIG. 3.
Figure 5:
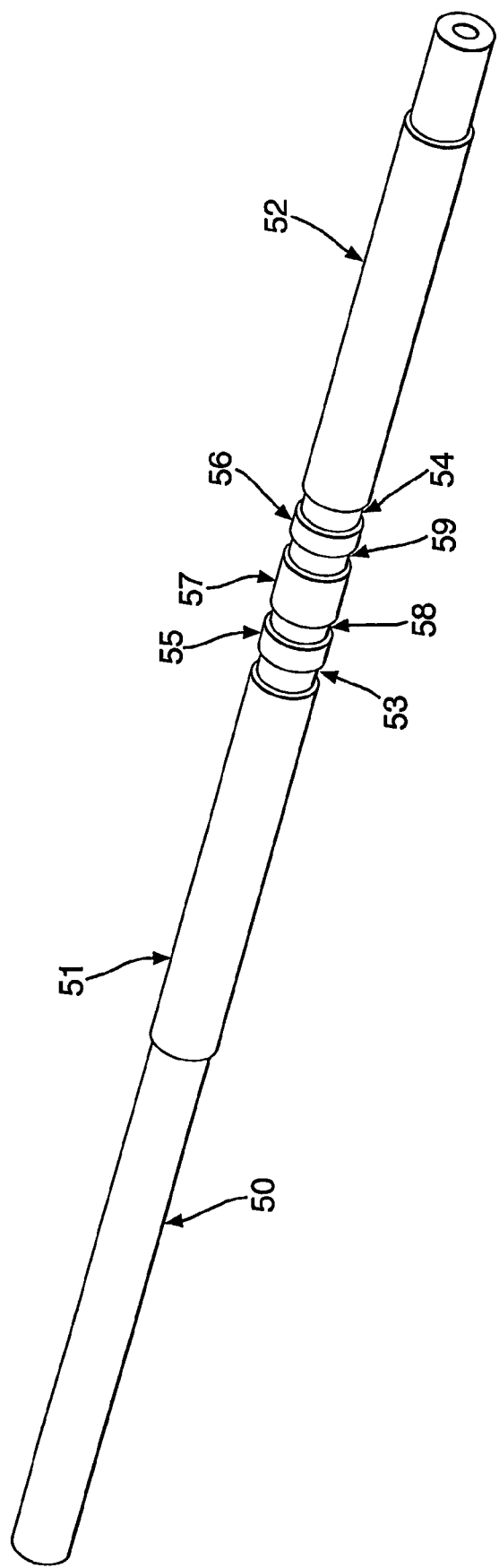
FIG. 5 is a perspective view of a tube from the unit of FIG. 4.

Each of the recesses 22 in the block 20 contains a charge sensor 40 of the kind shown in more detail in FIGS. 4 and 5. Each sensor 40 includes a rectangular upper plate 41 and a smaller lower plate 42 separated from one another by two support pillars 43 and 44. An O-ring seal 45 extends around the upper plate 41 to form an hermetic seal with a respective recess 22, the sensor 40 being held in place by screws extending into tapped holes (not shown) in the block 20 through two screw holes 46 at opposite ends of the plate. The upper plate 41 has an air pipe 47 (FIG. 4). On the underside of the plate 41 the pipe 47 supports and connects with the upper end of a charge sensor tube 50, which is shown in more detail in FIG. 5. The lower end of the charge sensor tube 50 is supported in a recess 70 in the lower plate 42. The recess 70 is circular and tapers to a reduced diameter at its lower end to reduce stray capacitance between the metal structure and electrodes on the charge sensor tube 50. The upper plate 41 also supports an electrical connector 49 connected to electrodes on the tube 50.

The tube 50 is shown in more detail in FIG. 5 and is of an electrically-insulative material such as glass or ceramic, it has a circular section with an outside diameter of about 1 mm, an inside diameter of about 0.5 mm and a length of about 30 mm. The tube 50 has five ring-shape electrodes on its outer surface spaced from one another along the length of the tube. The electrodes are on the outside of the tube because the air flowing through it may be humid and conductive. Two electrodes 51 and 52 at opposite ends of the tube 50 are each 8 mm long and are separated by insulating gaps 53 and 54, each 0.5 mm long, from two intermediate electrodes 55 and 56, which are each 0.5 mm long. A central electrode 57, which is 1 mm long, is separated from the intermediate electrodes by insulating gaps 58 and 59, each 0.5 mm long. The two outer electrodes 51 and 52 are connected to ground. The two intermediate electrodes 55 and 56 are connected together and the signal on these is subtracted from the signal on the central electrode 57 using the circuit shown in FIG. 7. The lower end of the tube 50 extends through the recess 70 and through a circular boss 60 formed on the lower surface of the lower plate 42. The electrodes 51, 52, 55, 56 57 are located towards the lower end of the tube 50 so that the distance between the charge measurement electrodes 55, 56 and 57 and the particles' size measurement at the end of the tube is kept to a minimum The circuit for each sensor 40 comprises two identical amplifying circuits 61 and 62 connected to the central electrode 57 and the intermediate electrode pair 55 and 56 respectively. Each amplifying circuit 61 and 62 includes a low-noise charge amplifier 63, a low pass filter 64, a second amplifier 65 and an analogue-to-digital converter 66. The digital output from each circuit 61 and 62 is supplied to a subtracting unit 67, which provides an output signal to a digital processor 68 with suitable processing to reduce noise. The processor 68 receives nine other inputs from the other nine sensor units 40 The output signal from each sensor unit 40 takes the form shown in FIG. 6.

In operation, atmospheric air is drawn into and through the apparatus by a pump (not shown) located on the outlet side. The air is preconditioned with an elutriation filter of known kind to remove particles outside the range 1 μm to 10 μm. Particles that are too small would give rise to noise; particles that are too large would risk clogging the tubes 50. It is important that the technique used to remove particles outside the desired size range has only a minimal effect on the charge of the remaining particles.

Figure 6:
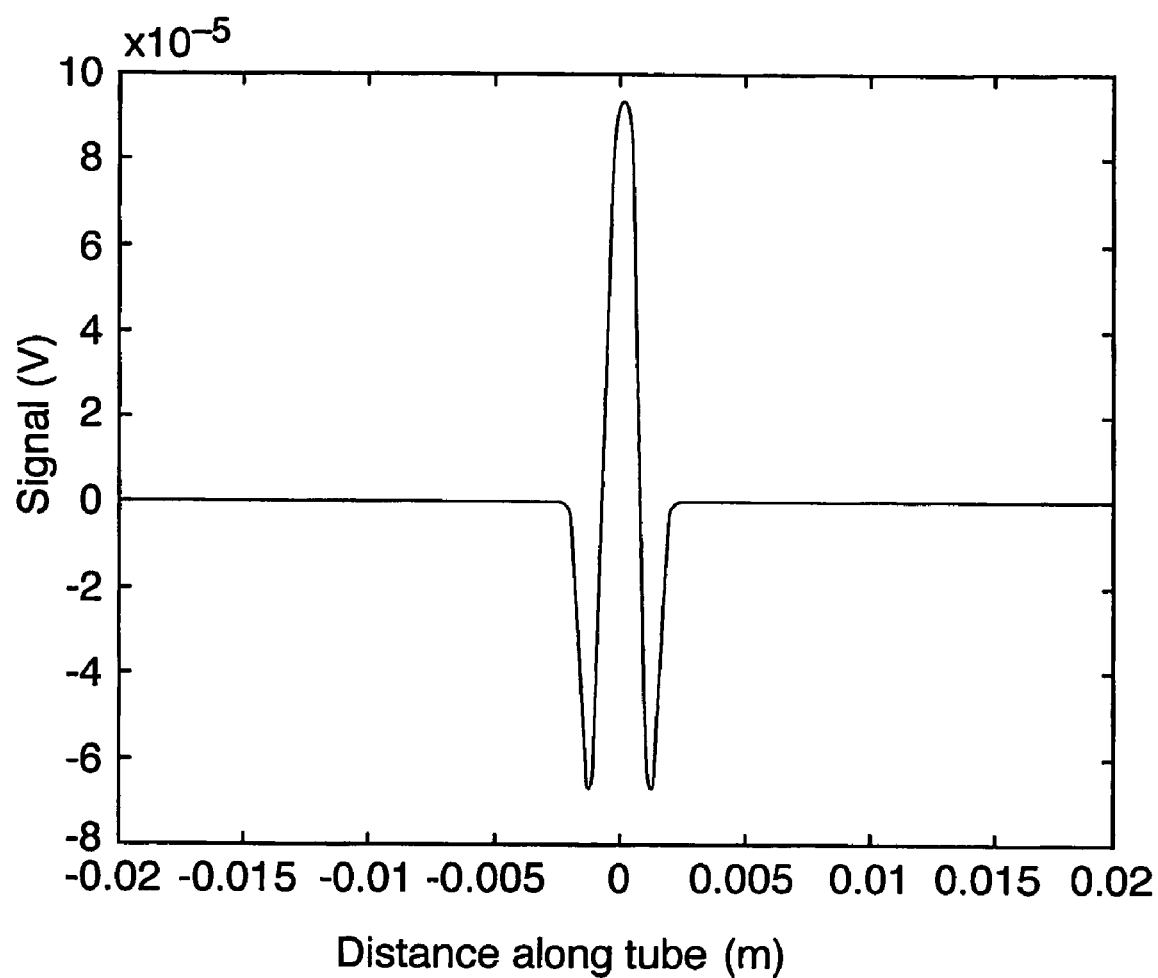
FIG. 6 is a graph showing the voltage output of the charge measuring unit.
Figure 7:
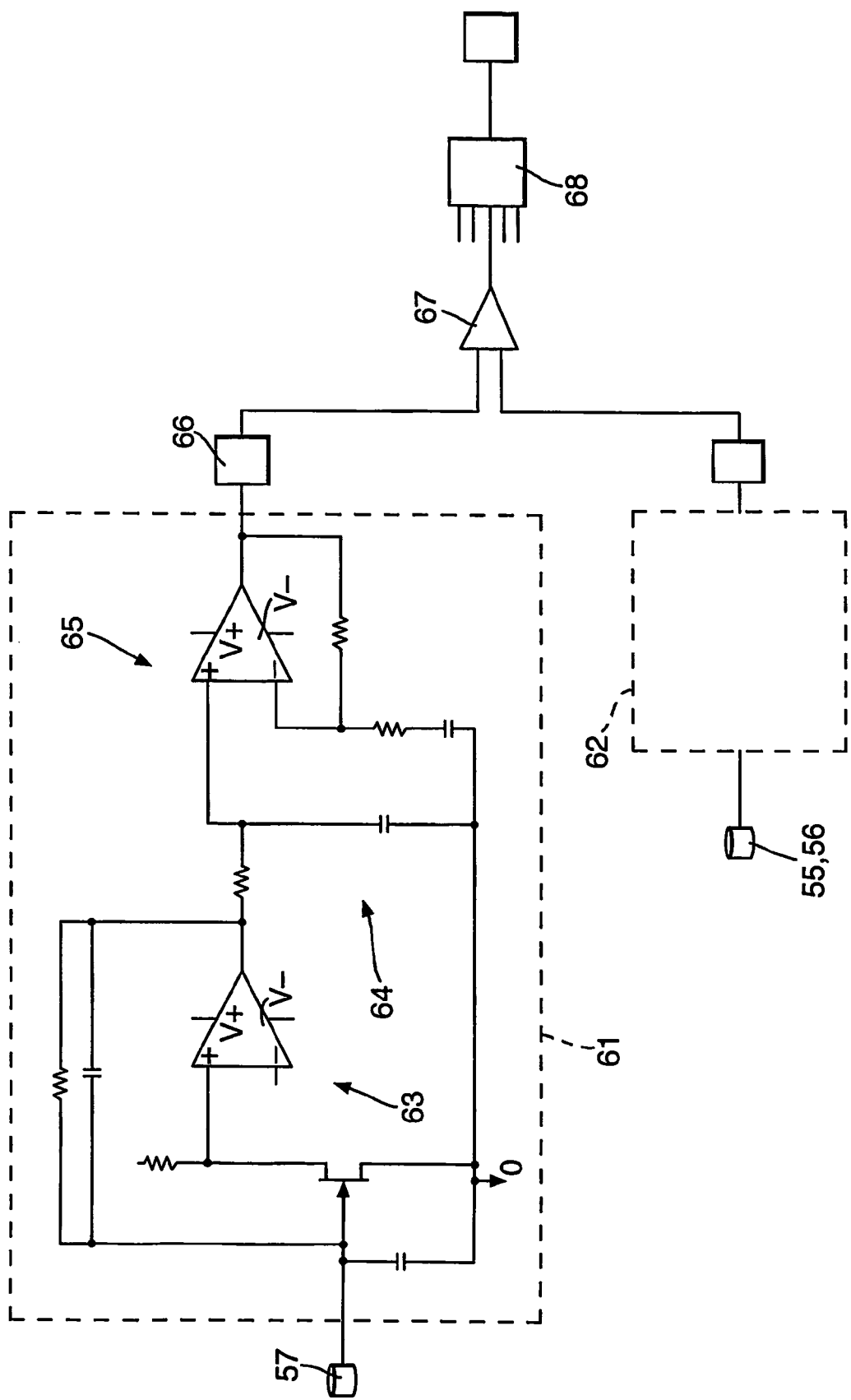
FIG. 7 is a diagram illustrating the electrical circuit of the apparatus.

The preconditioned air containing suspect particles flows to the charge sensing tubes 50 in each of the ten sensors 40. With a flow rate of about 10 L/min through the apparatus, the flow rate through each tube 50 is about 100 m/sec. When a particle is present in the air flowing through a sensor 40 an output response of the kind shown in FIG. 6 is produced. It can be seen that the width of the pulse P produced is highly constrained. The width of the pulse P depends on the diameter of the electrode rings 51, 52, 55, 56 and 57 with larger diameters producing a more spread out signal. Short duration pulses are important if the apparatus is to be able to provide reliable identification when there is a high throughput of particles. The magnitude of the pulse P depends on the charge on the particle. The output from the sensors 40 is supplied to the processor 68, which adds a timestamp to the data and is then stored to hard disc. The laser size measuring arrangement 10 continuously transmits a beam of laser radiation from the laser tube 11, which is directed along the groove 27 in the block 20 where it intersects particles emerging from the lower end of the tubes 50. The output of the PMT 23 is dependent on the size of the particle and this output is also supplied to the processor 68. The processor 68, therefore, receives information about the charge and size of each particle detected. This is compared with stored information to provide an output indicative of the nature of the particles.

It is believed that particles, in particular biological particles, carrying a relatively high electrical charge are more likely to have been generated artificially, and therefore present a possible hazard, because the usual mechanisms for producing small particles, such as aerosol nozzles and the like involve impact at high velocity. This causes disruption of the molecules, typically resulting in a charge on the particles.

The dimensions of the tube can be varied but its diameter should be as small as possible compatible with producing flow through it sufficient to avoid clogging. It is believed that the minimum practical internal diameter is about 500 μm, with a wall thickness of about 250 μm. The number of charge sensors can be varied in order to achieve the desired throughput.

One possible problem with the charge sensor tubes is that the particles may interact with the inside of the tubes to produce tribocharging. Glass and ceramic are known to have a fairly high propensity to tribocharging, although this is dependent on the nature of the particles. One possible alternative material is Mylar (a Registered Trade Mark of E. I. Du Pont de Nemours and Company), which is a polyester film material close to neutral in the triboelectric series, although this is only presently available in film form.

Instead of using an optical size measuring technique to identify a second characteristic of the particles it may be possible to identify the nature of particles from their charge and some other characteristic.

The invention claimed is:

1. An apparatus for characterizing a particle, wherein the apparatus comprises
    (a) an electrical charge sensor adapted to determine an electrical charge on the particle, wherein the electrical charge sensor includes a pathway for the particle and a plurality of electrodes spaced along the pathway arranged to provide an electrical output as the particle passes along the pathway, wherein the outermost electrodes are grounded, wherein two electrodes adjacent to outermost two electrodes are interconnected, and wherein a signal is derived from the difference between the central electrode and the two interconnected electrodes and;
    (b) an optical device adapted to determine a second characteristic of the particle, wherein the apparatus is adapted to provide an indication of the nature of the particle according to the charge and the second characteristic.

2. The apparatus according to claim 1, wherein the second characteristic is size.

3. The apparatus according to claim 1, wherein the pathway is provided by an electrically insulative tube and, wherein the plurality of electrodes are provided on an external surface of the tube.

4. The apparatus according to claim 3, wherein the tube has an internal diameter of substantially 0.5 mm.

5. The apparatus according to claim 3, further comprising a filter adapted to prevent particles greater than substantially 10 μm from entering the tube.

6. The apparatus according to claim 1, wherein there are five electrodes spaced along the pathway.

7. An apparatus for measuring a charge on a particle, wherein the apparatus comprises a tube comprising a first end and a second end along which the particle is arranged to flow, a first and a second outer electrode, wherein the first outer electrode is located adjacent to the first end and the second outer electrode is located adjacent to the second end, a third electrode adjacent to the first outer electrode and a fourth electrode adjacent to the second outer electrode, a fifth electrode located between the third and fourth electrodes, a connection connecting the first and second outer electrodes to ground, a connection connecting the third electrode to the fourth electrode and connecting the connected third and the fourth electrodes to a measuring circuit, and a connection connecting the fifth electrode to the measuring circuit, wherein the measuring circuit is adapted to subtract the signals on the third and fourth electrodes from the signal on the fifth electrode to derive a signal indicative of the charge on the particle.

* * * * *

UNITED STATES PATENT AND TRADEMARK OFFICE
CERTIFICATE OF CORRECTION

PATENT NO. : 7,298,127 B2  
APPLICATION NO. : 10/595082  
DATED : November 20, 2007  
INVENTOR(S) : Roger F. Golder, Roger F. Sewell and Danielle E. Toutoungi Page 1 of 1

It is certified that error appears in the above-identified patent and that said Letters Patent is hereby corrected as shown below:

On the Title Page, should read

Item -- (73) Assignee: Smiths Detection – Watford Limited, London (GB) --

Signed and Sealed this

Fifteenth Day of April, 2008

JON W. DUDAS  
*Director of the United States Patent and Trademark Office*